(12) United States Patent
Littlefair et al.

(10) Patent No.: US 10,524,885 B2
(45) Date of Patent: Jan. 7, 2020

(54) METHODS AND APPARATUS FOR DIGITAL IMAGING OF DENTAL MODELS

(71) Applicant: JESSI LEW PTY LIMITED, New South Wales (AU)

(72) Inventors: Darren Littlefair, Glenmore Park (AU); Georges Sara, Whale Beach (AU)

(73) Assignee: JESSI LEW PTY LIMITED, Homebush, New South Wales (AU)

( * ) Notice: Subject to any disclaimer, the term of this patent is extended or adjusted under 35 U.S.C. 154(b) by 32 days.

(21) Appl. No.: 16/063,941

(22) PCT Filed: May 23, 2017

(86) PCT No.: PCT/AU2017/050481
§ 371 (c)(1),
(2) Date: Jun. 19, 2018

(87) PCT Pub. No.: WO2017/201572
PCT Pub. Date: Nov. 30, 2017

(65) Prior Publication Data
US 2019/0336253 A1  Nov. 7, 2019

(30) Foreign Application Priority Data
May 23, 2016  (AU) ................ 2016901946

(51) Int. Cl.
*G06K 9/00* (2006.01)
*A61C 9/00* (2006.01)
(Continued)

(52) U.S. Cl.
CPC ............ *A61C 9/0053* (2013.01); *A61C 7/002* (2013.01); *A61C 11/00* (2013.01); *A61C 13/34* (2013.01); *A61C 9/0093* (2013.01)

(58) Field of Classification Search
CPC ..... A61B 9/0053; A61B 9/0046; A61B 9/004; A61B 9/0086; A61B 9/006; A61B 9/0093;
(Continued)

(56) References Cited

U.S. PATENT DOCUMENTS 7,702,492 B2 * 4/2010 Marshall ................ G06T 17/00
433/68
8,491,306 B2 * 7/2013 Raby ..................... A61C 7/146
433/213
(Continued)

FOREIGN PATENT DOCUMENTS

DE  102008060504 A1 * 6/2009 ............. A61C 11/00
DE  102008060504 A1    6/2009
(Continued)

OTHER PUBLICATIONS

Sun et al., "Evaluation of the Accuracy of Three-dimensional Reconstruction of Edentulous Model Jaw Relation Based on Dental Articulator Positioning", 2013 IEEE International Conference on Imaging Systems and Techniques, Oct. 2013, pp. 1-5. (Year: 2013).*

*Primary Examiner* — Jose L Couso
(74) *Attorney, Agent, or Firm* — Andrew H. Berks; Berks IP Law PLLC

(57) ABSTRACT

A dental method and associated apparatus is disclosed in which a navigation body, comprising a plurality of navigation elements, is scanned using a scanner. Relative locations of the navigation elements are determined and, based on the relative locations, a scanner coordinate system is determined. A dental model is also scanned using the scanner to obtain three-dimensional virtual image data of the dental model and the scanner coordinate system is associated with the image data. A three-dimensional virtual image of the dental model is positioned, based on the three-dimensional virtual image data, within a three-dimensional virtual scene.

(Continued)

The virtual scene is associated with a virtual articulator coordinate system, and the positioning of the virtual image within the virtual scene comprises positioning and orienting the virtual image relative to the virtual articulator coordinate system based on a transformation of the virtual image data from the scanner coordinate system to the virtual articulator coordinate system.

11 Claims, 9 Drawing Sheets

(51) Int. Cl.
    *A61C 11/00*     (2006.01)
    *A61C 7/00*     (2006.01)
    *A61C 13/34*     (2006.01)

(58) Field of Classification Search
    CPC ......... A61B 9/0066; A61B 7/002; A61B 7/08; A61B 7/146; A61B 11/00; A61B 11/001; A61B 11/087; A61B 11/08; A61B 11/005; A61B 13/34; A61B 13/0003; A61B 13/0004; A61B 13/097; A61B 13/0019; A61B 13/08; A61B 13/0022; A61B 13/0006; A61B 13/0013; A61B 19/045; A61B 19/05; A61B 19/04; A61B 5/77; A61B 5/4547; G16H 20/40; G16H 50/50; G06F 17/5009; G06F 17/50; G06F 3/0484; G06F 3/04815; G06F 3/04842; G06T 2207/30036; G06T 2207/10021; G06T 2207/10028; G06T 2207/30008; G06T 2207/10016; G06T 2207/10008; G06T 7/0012; G06T 7/248; G06T 7/66; G06T 2210/41; G06T 2219/2004; G06T 2219/004; G06T 2219/2016; G06T 17/00; G06T 15/205; G06T 19/003; G06T 19/20; G06T 1/0007; G06T 2200/08; Y10T 29/49567; G02B 27/22; G05B 2219/45167; G09B 23/283; G06G 7/48; H04N 1/0027; H04N 1/04; H04N 2005/2255; H04N 13/204; G01B 11/24; G01B 11/25; G06K 9/00201; G06K 9/42; G06K 9/6232; B33Y 50/00; B33Y 80/00; B33Y 10/00; B33Y 30/00

See application file for complete search history.

(56) References Cited

U.S. PATENT DOCUMENTS

| | | | |
|---|---|---|---|
| 10,426,574 B2 * | 10/2019 | Raby | A61C 7/20 |
| 2004/0172150 A1 * | 9/2004 | Perot | A61C 9/004 700/98 |
| 2005/0070782 A1 * | 3/2005 | Brodkin | A61C 13/0004 600/407 |
| 2007/0190492 A1 * | 8/2007 | Schmitt | A61C 13/0004 433/213 |
| 2007/0292004 A1 * | 12/2007 | Peters | A61C 19/045 382/120 |
| 2008/0057466 A1 * | 3/2008 | Jordan | A61C 11/00 433/69 |
| 2009/0284755 A1 * | 11/2009 | Friemel | G01B 11/24 356/601 |
| 2009/0305185 A1 * | 12/2009 | Lauren | A61C 11/00 433/29 |
| 2010/0240001 A1 * | 9/2010 | Steger | A61C 11/00 433/54 |
| 2012/0179281 A1 * | 7/2012 | Steingart | A61C 13/0004 700/97 |
| 2013/0066598 A1 * | 3/2013 | Fisker | A61C 11/00 703/1 |
| 2014/0242539 A1 * | 8/2014 | Fisker | A61C 13/0004 433/54 |
| 2014/0308623 A1 * | 10/2014 | Chang | A61C 13/0022 433/29 |
| 2015/0289954 A1 * | 10/2015 | Chang | A61C 13/0006 433/29 |
| 2016/0008111 A1 * | 1/2016 | Jumpertz | A61C 9/006 348/46 |
| 2016/0324605 A1 * | 11/2016 | Fisker | A61C 9/0053 |
| 2017/0165042 A1 * | 6/2017 | Hillukka | A61B 5/4542 |
| 2017/0273762 A1 * | 9/2017 | Fisker | A61C 11/00 |
| 2017/0312065 A1 * | 11/2017 | Marshall | A61B 34/20 |
| 2018/0110603 A1 * | 4/2018 | Stipek, Sr. | A61C 11/06 |
| 2018/0206959 A1 * | 7/2018 | Ohtake | A61C 11/00 |
| 2019/0290408 A1 * | 9/2019 | Fisker | A61C 11/00 |

FOREIGN PATENT DOCUMENTS

| | | |
|---|---|---|
| WO | 1999/015100 A1 | 4/1999 |
| WO | 2002/102270 A1 | 12/2002 |
| WO | 2011/103876 A1 | 9/2011 |
| WO | 2012/140021 A2 | 10/2012 |
| WO | 2015/101526 A1 | 7/2015 |

* cited by examiner

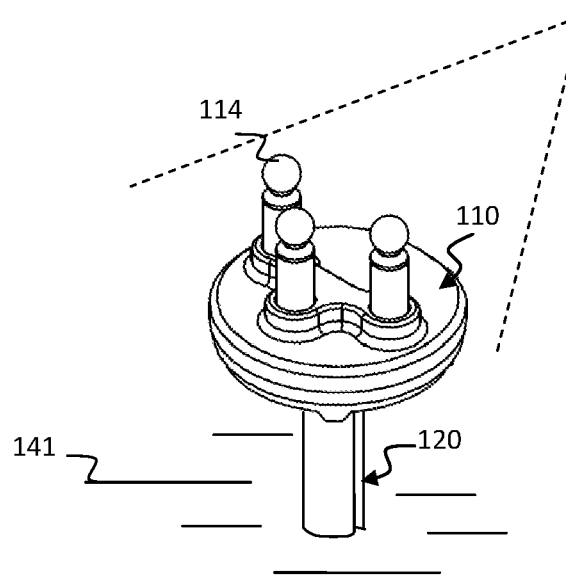
*Fig. 6*
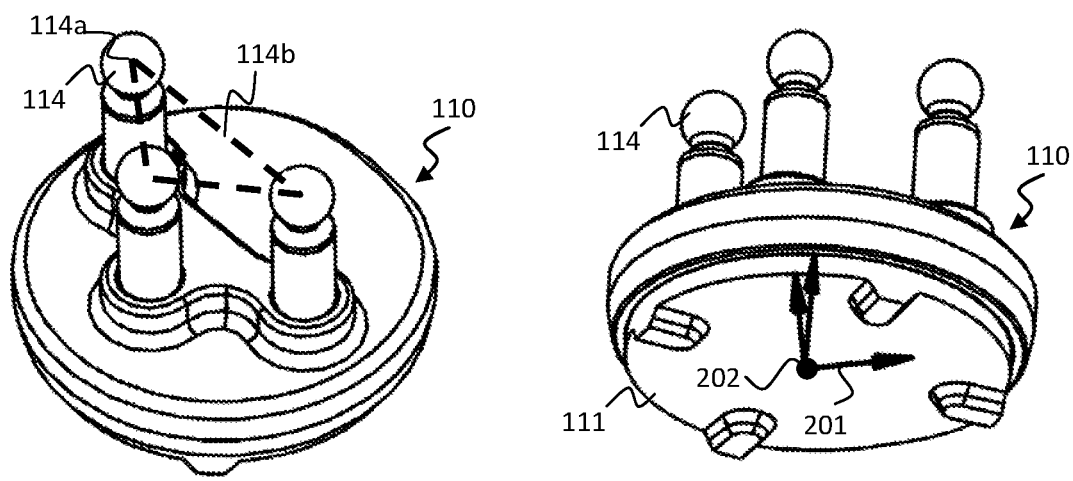
*Fig. 7a*        *Fig. 7b*

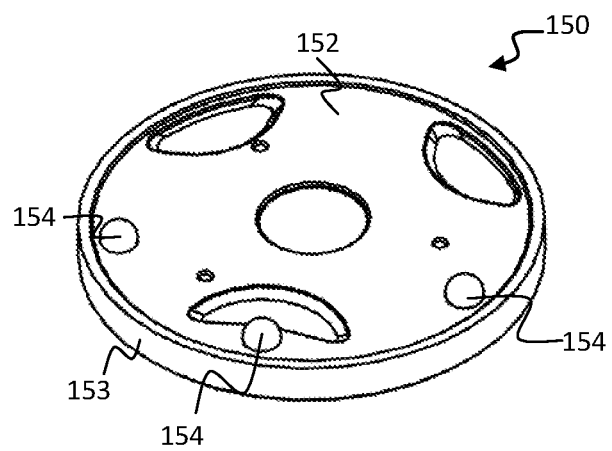
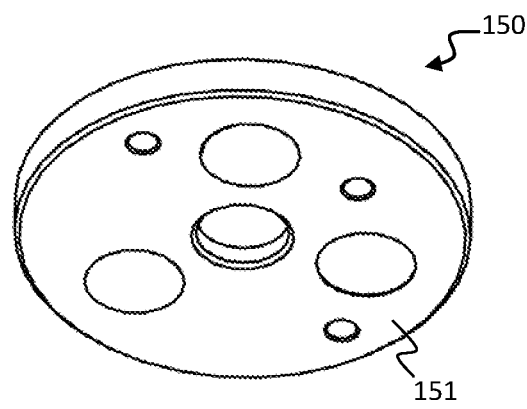
*Fig. 14a*      *Fig. 14b*
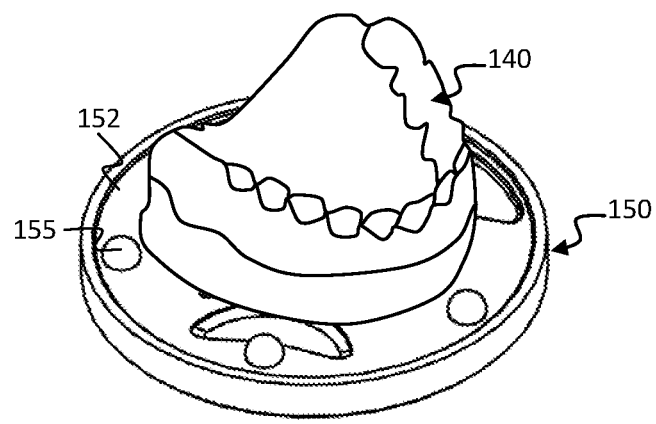
*Fig. 14c*

METHODS AND APPARATUS FOR DIGITAL IMAGING OF DENTAL MODELS

CROSS-REFERENCE TO RELATED APPLICATION

This application is the U.S. National Stage of PCT International Patent Application No. PCT/AU2017/050481, filed May 23, 2017, which claims priority to Australian Application No. 2016901946, filed May 23, 2016 the disclosures of each of which are incorporated herein by reference in their entities.

TECHNICAL FIELD

The present disclosure relates to digital imaging of dental models.

BACKGROUND

Dental models enable a dentist to understand how a patient's teeth and bite function in a static and/or dynamic relationship.

Dental models can be obtained by taking dental impressions in the patient's oral cavity, including of the patient's dentition and of the surrounding soft tissue. The dental impressions can be used to form casts of the dentition and tissue, which casts provide a form of dental model usable in many dental procedures such as diagnostics, treatment planning, and prosthesis design and fabrication, for example.

Recent advances in dental technology have progressed from conventional techniques, where design and fabrication of dental prostheses take place only in the physical world, to computer-based techniques, where these processes are carried out at least partly in a virtual realm. In the latter, the dental models are digitally reproduced via an imaging process employing imaging apparatus such as a dental model scanner. Based on the digitally reproduced dental models, prosthesis design processes can be carried out at least partly using 3D computer-aided-design (CAD) or other computer design techniques. This can reduce total reliance on the physical dental models in the preparation and testing of prosthesis designs.

One feature of conventional prosthesis design is the articulating together of dental models to reproduce and study the bite of the patient. This is commonly carried out using an articulator that includes an upper jaw plate and a lower jaw plate on which upper and lower dental models are mounted, respectively, and includes a hinge mechanism that replicates the hinge axis of the mandibular condyles.

It is desirable to accurately replicate features of the articulator, with dental models mounted thereon, in a virtual realm.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to an aspect of the present disclosure, there is provided a dental method comprising:

scanning a first navigation body using a scanner, the first navigation body comprising a plurality of first navigation elements;

determining the relative locations of the first navigation elements and, based on the relative locations of the navigation elements, determining a first scanner coordinate system;

scanning a first dental model using the scanner to obtain three-dimensional virtual image data of the first dental model and associating the first scanner coordinate system with the image data; and positioning a three-dimensional virtual image of the first dental model, based on the three-dimensional virtual image data, within a three-dimensional virtual scene, wherein the three-dimensional virtual scene is associated with a first virtual articulator coordinate system, and wherein the positioning of the virtual image of the first dental model within the virtual scene comprises positioning and orienting the virtual image of the first dental model relative to the first virtual articulator coordinate system based on a transformation of the virtual image data of the first dental model from the first scanner coordinate system to the first virtual articulator coordinate system.

According to an aspect of the present disclosure, there is provided a dental method comprising:

receiving three-dimensional virtual image data of a first dental model, the three-dimensional virtual image data of the first dental model having been obtained by scanning the first dental model using a scanner, the three-dimensional virtual image data of the first dental model being associated with a first scanner coordinate system, the first scanner coordinate having been determined by scanning a first navigation body that comprises a plurality of first navigation elements, determining the relative locations of the first navigation elements and, based on the relative locations of the navigation elements, determining the first scanner coordinate system;

positioning a three-dimensional virtual image of the first dental model, based on the three-dimensional virtual image data, within a three-dimensional virtual scene;

wherein the three-dimensional virtual scene is associated with a first virtual articulator coordinate system, and wherein the positioning of the virtual image of the first dental model within the virtual scene comprises positioning and orienting the virtual image of the first dental model relative to the first virtual articulator coordinate system based on a transformation of the virtual image data of the first dental model from the first scanner coordinate system to the first virtual articulator coordinate system.

According to another aspect of the present disclosure, there is provided software that, when installed on a computing device, causes the computing device to perform the method of the immediately preceding aspect.

According to another aspect of the present disclosure, there is provided a dental apparatus comprising:

a scanner:

a first navigation body comprising a plurality of first navigation elements; and a processor, the processor being configured to:

receive a three-dimensional virtual image data of a first dental model, the three-dimensional virtual image data of the first dental model having been obtained by scanning the first dental model using the scanner, the three-dimensional virtual image data of the first dental model being associated with a first scanner coordinate system, the first scanner coordinate having been determined by scanning the first navigation body, determining the relative locations of the first navigation elements and, based on the relative locations of the navigation elements, determining the first scanner coordinate system; and position a three-dimensional virtual image of the first dental model, based on the three-dimensional virtual image data, within a three-dimensional virtual scene relating to an articulator, wherein the three-dimensional virtual scene is associated with a first virtual articulator coordinate system, and wherein the positioning of the virtual image of the first dental model within the virtual scene comprises positioning and orienting the virtual image of the first dental model relative to the first virtual articulator coordinate system based on a transformation of the virtual image data of the first dental model from the first scanner coordinate system to the first virtual articulator coordinate system.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In any of the aspects disclosed herein, the first navigation body may be connected to the first dental model. For example, the first dental model may be mounted on the first navigation body. The first navigation body and the first dental model may be collectively mounted to a connector in the dental scanner, prior to and during the scanning. By having the first dental model connected to the first navigation body, the scanning of the first navigation body and the scanning of the first dental model may take place at the same time. Thus, the relative locations of the navigation elements, and thus the first scanner coordinate system, may be determined substantially at the same time as the three-dimensional virtual image data of the first dental model is obtained.

Alternatively, the first navigation body may be provided separately from the dental model. The first navigation body may be mounted to the connector in the dental scanner and scanning carried out to determine the first scanner coordinate system. After or before this scanning step, the first dental model may be mounted to the same connector and scanning carried out to obtain the three-dimensional virtual image data. Since the first navigation body and first the dental model are mounted to the same connector during their respective scans, the first scanner coordinate system can be applied to the three-dimensional virtual image data, essentially replicating the one-step approach to scanning described above. When the first navigation body is provided separately from the first dental model, the first dental model may be mounted on a first support body, and the first dental model and first support body may be collectively mounted to the connector of the scanner.

When the first navigation body is scanned, the first navigation elements may be in a predetermined position and orientation relative to a first scanner datum point. When the first navigation body is located in the scanner, the first scanner datum point may align with a point in or on the first navigation body or otherwise. The first scanner coordinate system that is determined may be positioned at the first scanner datum point. For example, the origin or '0,0,0' point of the scanner coordinate system may be positioned at the first scanner datum point.

When the first dental model is scanned, the location of the first scanner datum point may be identified within the three-dimensional virtual image data of the first dental model the and the first scanner coordinate system may be associated accordingly with the three-dimensional virtual image data.

The first virtual articulator coordinate system may be positioned at a first virtual articulator datum point. The origin or '0,0,0' point of the first virtual articulator coordinate system may be the first virtual articulator datum point. When the virtual image of the dental model is positioned in the virtual scene, the first scanner datum point within the three-dimensional virtual image data may be aligned with the first virtual articulator datum point, and the axes of the first scanner coordinate system, and thus the virtual image of the first dental model, may be rotated to align with the axes of the first virtual articulator coordinate system. The first scanner datum point may be aligned with the first virtual articulator datum point by being positioned exactly upon the first virtual articulator datum point or by being positioned at a predetermined distance from the first virtual articulator datum point.

The three-dimensional virtual scene can relate to a virtual articulator. The virtual articulator may be representative of a physical (real-world) articulator. The three-dimensional virtual scene can relate to the virtual articulator by being associated with at least the first articulator coordinate system and by including data relating to one or more components of the virtual articulator. For example, the virtual scene may include data indicating one or more of: the relative locations of all or part of a virtual lower jaw and/or a virtual upper jaw of the articulator; the shape and dimensions of all or part of the virtual lower jaw and/or the virtual upper jaw of the articulator; a virtual hinge position (hinge axis) of the articulator; and a virtual pin position of the articulator. Moreover, the data may include one or more rules of movement and interaction between these virtual components of the articulator. The virtual scene may be configured so that, when the three-dimensional virtual image of the first dental model is positioned within the virtual scene, the three-dimensional virtual image of the first dental model may be manipulated within the virtual scene in a manner representative of how the first dental model may be manipulated when mounted on the corresponding physical articulator.

Some or all of the information relating to the articulator may be represented visually and/or non-visually in the virtual scene. Where information is represented visually, for example, the three-dimensional virtual scene may comprise a three-dimensional image of at least part of the articulator. The three dimensional image of at least part of the articulator may comprise one or more of: a portion of the virtual lower jaw of the articulator (e.g. a lower jaw plate); a portion of the virtual upper jaw of the articulator (e.g. an upper jaw plate); the virtual hinge position (hinge axis) of the articulator; and the virtual pin position of the articulator. The image may provide true (lifelike) virtual representations of these portions of the articulator, or may provide abstract or generalised virtual representations of these portions of the articulator.

The first virtual articulator datum point may be positioned at one of the virtual upper jaw and the virtual lower jaw. Thus, by aligning the first scanner datum point with the first virtual articulator datum point, the virtual image of the first dental model may be located on, or at least adjacent, a specific one of the virtual upper jaw and the virtual lower jaw within the virtual scene.

The method may comprise replicating some or all of the above steps with two or more additional dental models. For example, in one embodiment, the method may comprise replicating some or all of the above steps at least with a second dental model. One of the first and second dental models may be a dental model based on the lower jaw of the patient and which is to be located at the virtual lower jaw of the virtual articulator, and the other of the first and second dental models may be a dental model based on the upper jaw of the patient and which is to be located at the virtual upper jaw of the virtual articulator. The following discussions set forth method steps in relation to a second dental model, but the methods steps can apply, mutatis mutandis, to any number of additional dental models.

The method may comprise scanning the second dental model using the scanner to obtain three-dimensional virtual image data of the second dental model and associating the image data either with the first scanner coordinate system or with a different, second scanner coordinate system.

The method may comprise positioning, in the virtual scene, a three-dimensional virtual image of the second dental model, based on three-dimensional virtual image data of the second dental model. Three-dimensional virtual images of the first and second dental models may therefore be provided in the same virtual scene.

The method may comprise associating the first scanner coordinate system with the three-dimensional virtual image data of the second dental model, e.g., if the first and second dental models are mounted (in turn) to the same connector within the scanner when they are scanned. By being mounted to the same connector, the same scanner coordinate system can be applicable to both models. Nevertheless, it may be advantageous to determine a second scanner coordinate system, e.g., to maintain a high level of accuracy over time. If environmental factors in the scanner change, e.g., as a result of placing different dental models in the scanner, determining a second scanner coordinate system that is specific to the second dental model can improve accuracy. Changes in environmental factors can include slight movements in the connector on which the dental models are mounted, or relative movement of other scanner parts.

When a second scanner coordinate system is used, the method may comprise scanning again the first navigation body using the scanner and determining the second coordinate system in the same manner that the first coordinate system is determined. Alternatively, a second navigation body may be used, the method comprising scanning the second navigation body using the scanner, the second navigation body comprising a plurality of second navigation elements; determining the relative locations of the second navigation elements and, based on the relative locations of the second navigation elements, determining the second scanner coordinate system.

The second dental model may be connected to the first navigation body or, when used, to the second navigation body. For example, the second dental model may be mounted on the respective navigation body. The navigation body and the second dental model may be collectively mounted to a connector in the dental scanner, prior to and during the scanning, e.g., the same connector as used with respect to the first dental model. By having the second dental model connected to the navigation body, the scanning of the navigation body and the scanning of the second dental model may take place at the same time. Thus, the relative locations of the navigation elements, and thus the second scanner coordinate system, may be determined substantially at the same time as the three-dimensional virtual image data of the second dental model is obtained.

Alternatively, the first navigation body or, when used, second navigation body, may be provided separately from the second dental model. The first or second navigation body may be mounted to a connector in the dental scanner and scanning carried out to determine the second scanner coordinate system. After or before this scanning step, the second dental model may be mounted to the same connector and scanning carried out to obtain the three-dimensional virtual image data. Since the navigation body and second the dental model are mounted to the same connector during their respective scans, the second scanner coordinate system can be applied to the three-dimensional virtual image data, essentially replicating the one-step approach to scanning described above. When the navigation body is provided separately from the second dental model, the second dental model may be mounted on a support body, e.g., the first support body or a further, second support body. The second dental model and the support body may be collectively mounted to the connector of the scanner.

When the first or second navigation body is scanned to obtain the second coordinate system, the navigation elements may be in a predetermined position and orientation relative to a second scanner datum point. When the first or second navigation body is located in the scanner, the second scanner datum point may align with a point in or on the navigation body or otherwise.

The second scanner coordinate system that is determined may be positioned at the second scanner datum point. For example, the origin or '0,0,0' point of the scanner coordinate system may be positioned at the second scanner datum point.

When the second dental model is scanned, the location of the second scanner datum point may be identified within the three-dimensional virtual image data of the second dental model and the second scanner coordinate system may be associated accordingly with the three-dimensional virtual image data of the second dental model.

To position the three-dimensional virtual image of the second dental model in the virtual scene, different approaches may be taken, but with each approach relying on a transformation of the virtual image data of the second dental model from the associated first or second scanner coordinate system to a corresponding articulator coordinate system.

In one approach, the virtual image data of the second dental model is transformed from the associated first or second scanner coordinate system to the first articulator coordinate system. However, a translation is applied to the virtual image data in order to shift the position of the virtual image of the second dental model so that it is adjacent an opposite one of the of the virtual upper and lower jaws from the virtual image of the first dental model. The translation may be based on a known distance between the upper and lower jaws of the articulator. The translation may place the virtual image of the second dental model at a second virtual articulator datum point.

In another approach, the virtual image data of the second dental model is transformed from the associated first or second scanner coordinate system to a second articulator coordinate system that can be associated with the virtual scene. The second virtual articulator coordinate system may be positioned at a second virtual articulator datum point. The origin or '0,0,0' point of the second virtual articulator coordinate system may be the second virtual articulator datum point. When the virtual image of the second dental model is positioned in the virtual scene, the scanner datum point within the three-dimensional virtual image data of the second dental model may be aligned with the second virtual articulator datum point and the axes of the associated scanner coordinate system, and thus the virtual image of the second dental model, may be rotated to align with the axes of the second virtual articulator coordinate system. The scanner datum point may be aligned with the second virtual articulator datum point by being positioned exactly upon the second virtual articulator datum point or by being positioned at a predetermined distance from the second articulator datum point.

The methods described above may accurately replicate, in a virtual scene, the positioning of dental models and relevant parts of an articulator, including the locations of the dental models relative to upper and/or lower jaws (e.g., upper and/or lower plates) of the articulator, and the relative positioning of the hinge axis. Accurately replicating features of the articulator means that any design processes carried out based on the visual scene can match and be subsequently tested on a corresponding physical articulator, for example.

In any of the aspects, herein, the navigation elements can comprise any types of navigation elements commonly used to determine points, directions or coordinates in scanning or image guided procedures, for example. To allow a three-dimensional coordinate system to be obtained, at least three navigation elements may be provided. The coordinate system may be calculated based on a notional plane extending between the at least three navigation elements, for example. The notional plane may define and extend through perpendicular x- and y-axes, for example. A third axis (e.g., a z-axis) can be determined that is perpendicular to the x- and y-axes. At least one of the navigation elements may be distinguishable from the other navigation elements, e.g. by being structurally different from (e.g., larger or smaller than) one or more others of the navigation elements or by being at an identifiable position of a notional triangle or other shape extending between the navigation elements. This may enable a specific location for the third axis (e.g., a z-axis) to be determined, which axis may extend through the distinguishable navigation element in a direction perpendicular to the x- and y-axes. Other known techniques to determine the locations of x-, y- and z-axes based on the positioning of navigation elements (markers) may be employed.

The navigation elements may comprise objections such as balls or spheres, for example. Additionally or alternatively, the navigation elements may comprise one or more surfaces of an object, e.g., one or more surfaces of a cube.

The first and/or second navigation bodies, on which the dental models may be mounted, or which may be used independently of the dental models, may each comprise an engagement surface for engaging with a receiving surface of the connector of the scanner. The first and/or second navigation bodies may each comprise a plate and the engagement surface may be located on an underside of the plate, for example. When a dental model is to be mounted on the navigation body, a topside of each plate may provide a support surface for engaging with the dental model. The navigation elements may project from the support surface or otherwise. When a dental model is located thereon, the navigation elements may be disposed to the sides, underneath and/or reach over the dental model, for example.

Similarly, the first and/or second support bodies, on which the dental models may alternatively be mounted, may each comprise an engagement surface for engaging with a receiving surface of the connector of the scanner. The first and/or second support bodies may each comprise a plate and the engagement surface may be located on an underside of the plate, for example. When a dental model is to be mounted on the support bodies, a topside of each plate may provide a support surface for engaging with the dental model. The engagement plates of the support bodies may be similar or identical to the engagement plates of the navigation bodies, but may not comprise any navigation elements.

Each engagement surface may comprise one or more recesses and/or one or more protrusions for engaging with complimentary protrusions and/or recesses of the receiving surface of the connector. The arrangement of recesses and protrusions may ensure that the dental models and/or navigation bodies are positionable at one desirable orientation on the connector only. Additionally or alternatively, the arrangement of recesses and protrusions may prevent sideways movement or slipping of the associated bodies from the connector.

The connector may comprise a mounting plate and the receiving surface may be located on a topside of the mounting plate. The mounting plate may be attached to a distal end of a post. The connector may be attached to a floor, rotatable platform or other surface of the scanner.

The connector may comprise one or more magnets. Similarly, the navigation bodies and/or support bodies may comprise one or more magnets that are attracted to the one or more magnets of the connector. Thus, a magnetic coupling may be provided between the connector and the navigation and/or support bodies. The magnetic coupling may ensure a firm but releasable attachment of the connector and the navigation and/or support bodies.

After positioning the three-dimensional virtual images of the first and optionally second dental models in the virtual scene, computer modeling, e.g., CAD, techniques may be employed to determine an appropriate configuration of a dental prosthesis for the patient, an appropriate dental treatment for the patient, or otherwise. During or subsequent to this procedure, the first and optionally second or further dental models that are scanned may be engaged with a physical (real-world) articulator on which the virtual articulator was based. The physical articulator may comprise receiving surfaces at an upper and lower jaw thereof for engaging the engagement surfaces of the navigation bodies and/or support bodies on which the dental models are mounted. The receiving surfaces of the physical articulator may have a profile and/or configuration that corresponds to a profile and/or configuration of the receiving surface of the connector of the scanner since they are adapted to engage with the same surfaces of the navigation or support bodies. The receiving surfaces of the physical articulator may be provided on mounting plates at the upper and lower jaws of the articulator. Moreover, the receiving surfaces of the physical articulator may comprise one or more magnets to enable magnetic coupling with the navigation and/or support bodies.

As indicated above, steps according to the present disclosure may be carried out on one or more computing devices and may generally employ one or more processors. It will be recognised that processors or processing apparatus as disclosed herein may comprise a number of control or processing modules for controlling one or more steps of the method and may also include one or more storage elements, for storing desired data, e.g., data relating to a physical articulator and data related to virtual representations of at least portions of the physical articulator, and data relating to the virtual dental models. The modules and storage elements can be implemented using one or more processing devices and one or more data storage units, which modules and/or storage devices may be at one location or distributed across multiple locations and interconnected by one or more communication links. Processing devices may include desktop computers, laptop computers, tablets, smartphones, personal digital assistants and other types of computing devices, including systems manufactured specifically for the purpose of carrying out methods according to the present disclosure.

Further, the processing modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g., RAM) and/or non-volatile (e.g., ROM, disk) memory or otherwise.

As indicated above, steps according to the present disclosure may comprise positioning, in a virtual scene, one or more three-dimensional virtual images of different features such as dental models and parts of an articulator. The virtual scene may be at least partially presented on a display such as a computer screen, tablet screen, smartphone screen or other types of displays suitable for presenting digital images.

In one aspect of the present disclosure there is provided a navigation body for use in the methods described above, the navigation body comprising a plurality of navigation elements. The navigation body may comprise any one or more features of the navigation bodies described above.

In another aspect of the present disclosure, there is provided a support body for use in the methods described above. The support body may comprise any one or more features of the support bodies described above.

In another aspect of the present disclosure, there is provided a connector for use in the methods described above. The connector may comprise any one or more features of the connector described above.

In another aspect of the present disclosure, there is provided an articulator for use in the methods described above. The articulator may comprise any one or more features of the articulator described above.

In another aspect of the present disclosure, there is provided a kit comprising two or more items selected from the navigation body, the support body, the connector and the articulator described above.

The navigation body, the support body, the connector and the articulator may comprise complimentary receiving and engaging surfaces. For example, the navigation body and the support body may each comprise an engagement surface that is appropriate to engage with a receiving surface of the connector and the articulator. The engagement surfaces of the navigation body and the support body may be substantially identical and the receiving surfaces of the connector and articulator may be substantially identical, for example.

BRIEF DESCRIPTION OF DRAWINGS

FIG. 6 shows a top oblique view of the navigation body of FIG. 1a mounted to the connector of FIG. 2 during scanning according to an embodiment of the present disclosure;

FIGS. 7a and 7b shows top and bottom oblique views, respectively, of the navigation body of FIGS. 1a and 1b alongside a notional triangle and a scanner coordinate system, respectively;

FIGS. 14a and 14b show top and bottom oblique views, respectively, of a navigation body according to another embodiment of the present disclosure, and FIG. 14c shows a top oblique view of the navigation body of FIG. 14a with a dental model mounted thereon.

DESCRIPTION OF EMBODIMENTS

Embodiments of the present disclosure relate to a dental method, and apparatus for use in the dental method, where one or more dental models are scanned and virtual images of the dental models are positioned in a virtual scene relating to an articulator.

The dental models can be obtained by taking dental impressions in a patient's oral cavity, including of the patient's dentition and of the surrounding soft tissue. The dental impressions can be used to form casts of the dentition and tissue, which casts provide the dental models, and which dental models are usable in one or more dental procedures such as diagnostics, treatment planning, and prosthesis design and fabrication.

Based on the virtual images of the dental models, prosthesis design processes can be carried using 3D computer-aided-design (CAD) or other computer design techniques such that reliance on the physical dental models in the preparation and testing of prosthesis designs can be reduced or even eliminated.

Figure 1A:
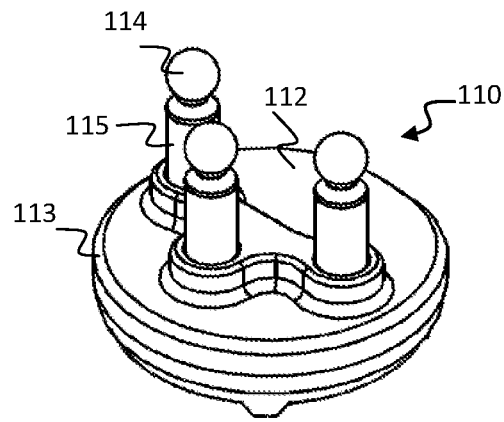
FIGS. 1a and 1b show top and bottom oblique views, respectively, of a navigation body according to an embodiment of the present disclosure.
Figure 1B:
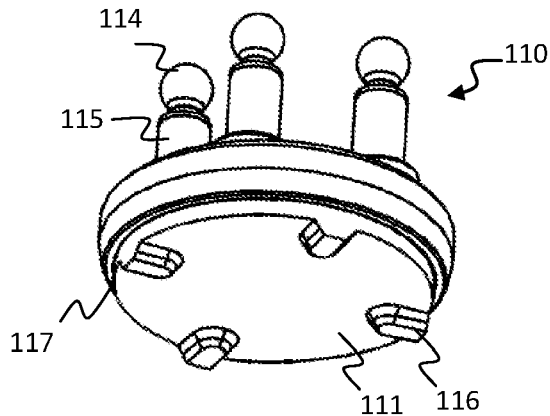

Referring to FIGS. 1a and 1b, apparatus according to an embodiment of the present disclosure includes a navigation body 110. The navigation body 110 has a generally plate-like configuration with an engagement surface 111 on a first side and a support surface 112 on a second side opposite to the first side. The navigation body 110 is substantially disk-shaped with a substantially circular periphery 113, although other shapes of the navigation body can be used (e.g., square, rectangular or otherwise).

The navigation body 110 includes a plurality of navigation elements and, more particularly, three navigation spheres 114. The navigation spheres 114 are mounted on respective pillars 115 that project from the support surface 112 of the navigation body 110. The three navigation spheres 114 are spaced from each other and positioned at the vertices of a notional triangle (see also FIG. 7a). While navigation spheres 114 are used in this embodiment, a variety of different types of navigation elements may be used.

Figure 2:
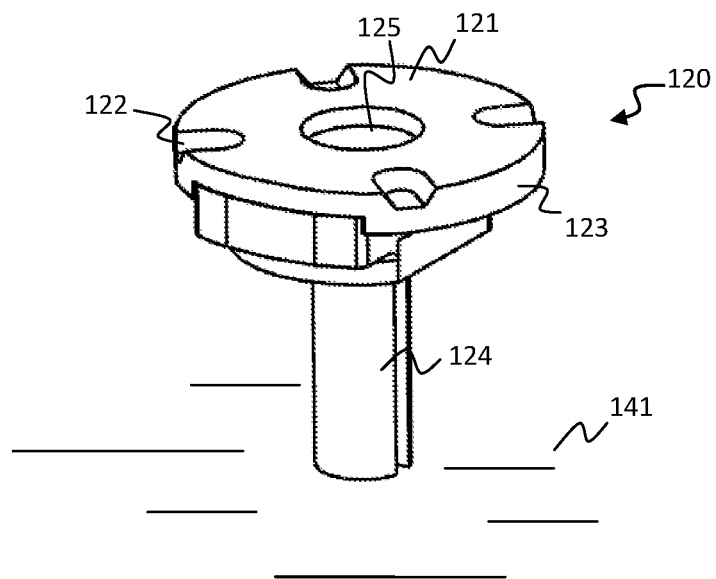
FIG. 2 shows a top oblique view of a connector according to an embodiment of the present disclosure.

The engagement surface 111 of the navigation body 110 is configured to engage with a receiving surface 121 of a connector 120 of a scanner, the connector 120 being illustrated in FIG. 2. The connector 120 can be located on a floor 141 or other surface of the scanner. The receiving surface 121 of the connector includes a plurality of recesses 122 for engaging with a plurality of complimentary protrusions 116 on the engagement surface 111 of the navigation body 110. The arrangement of protrusions 116 and recesses 122 ensures that the navigation body 110 is positionable at one desirable orientation on the connector 120 only and also limits or prevents lateral movement of the navigation body 110 relative to the connector 120 when engaged.

The receiving surface 121 of the connector 120 is provided by a topside of a mounting plate 123 of the connector 120. The mounting plate 123 is attached to a distal end of a post 124 that protrudes from the floor 141 of the scanner or other surface of the scanner. In alternative embodiments, the mounting plate 123 may be attached directly to the floor 141 (or other surface) of the scanner. In general, the connector 120 can hold the navigation body 110 securely, in a fixed location, in the scanner, while the navigation body 110 is being scanned by the scanner.

To further assist in securely locating the navigation body 110, the connector 120 includes a first magnet 125 at a central region of the receiving surface 121. A second magnet is provided by a magnetic metal layer 117 of the navigation body 110 that defines the engagement surface 111 of the navigation body 110. The first and second magnets 125, 117 are configured to attract each other, providing for a firm but releasable attachment between the navigation body 110 and the connector 120.

Figure 3A:
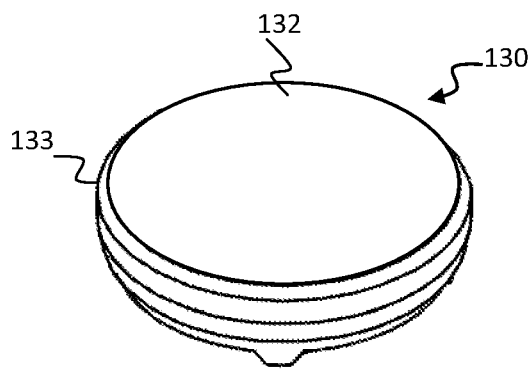
FIGS. 3a and 3b show top and bottom oblique views, respectively, of a support body according to an embodiment of the present disclosure.
Figure 3B:
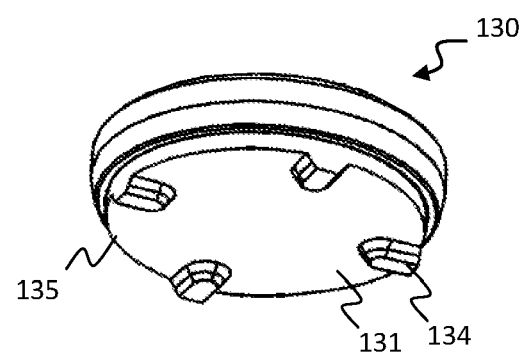

Referring to FIGS. 3a and 3b, the apparatus according to the present embodiment also includes a support body 130. The support body 130 has a generally plate-like configuration with an engagement surface 131 on a first side and a support surface 132 on a second side opposite to the first side. The support body 130 is substantially disk-shaped with a substantially circular periphery 133, although other shapes of the support body 130 can be used (e.g., square, rectangular or otherwise).

Figure 4:
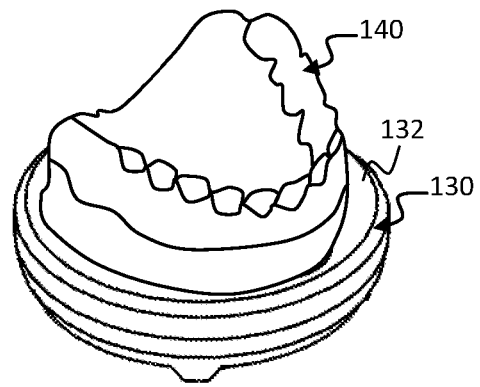
FIG. 4 shows a top oblique view of the support body of FIG. 3a with a dental model mounted thereon.

The support surface 132 of the support body is adapted to receive a dental model 140, as illustrated in FIG. 4, for example. The dental model 140 is glued or fixed by other means to the support surface 132. The dental model 140 shown in FIG. 4 is a cast of the gums and teeth of a lower jaw, although the dental model can take other configurations. For example, the dental model may be a cast of the gums only and/or of the upper jaw.

The engagement surface 131 of the support body 130 is also configured to engage with the receiving surface 121 of the connector 120 illustrated in FIG. 2. To facilitate the engagement, the engagement surface 131 of the support body 130 is configured in a substantially identical manner to the engagement surface 111 of the navigation body 110. For example, the engagement surface 131 of the support body 130 includes a plurality of protrusions 134 for engaging with the complimentary recesses 122 of the connector 120. The arrangement of protrusions 134 and recesses 122 ensures that the support body 130 is positionable at one desirable orientation on the connector 120 only and also limits or prevents lateral movement of the support body 130 relative to the connector 120 when engaged. In general, the connector 120 can hold the support body 130 securely, in a fixed location, in the scanner, while the support body 130 (and dental model located thereon) is being scanned by the scanner.

To further assist in securely locating the support body 130, a second magnet is also provided by a magnetic metal layer 135 of the support body 130 that defines the engagement surface 131 of the support body 130. As for the navigation body 110, the second magnetic 135 of the support body 130 is configured to be attracted to the first magnet 125 of the connector 120, providing for a firm but releasable attachment between the support body 130 and the connector 120.

Figure 5:
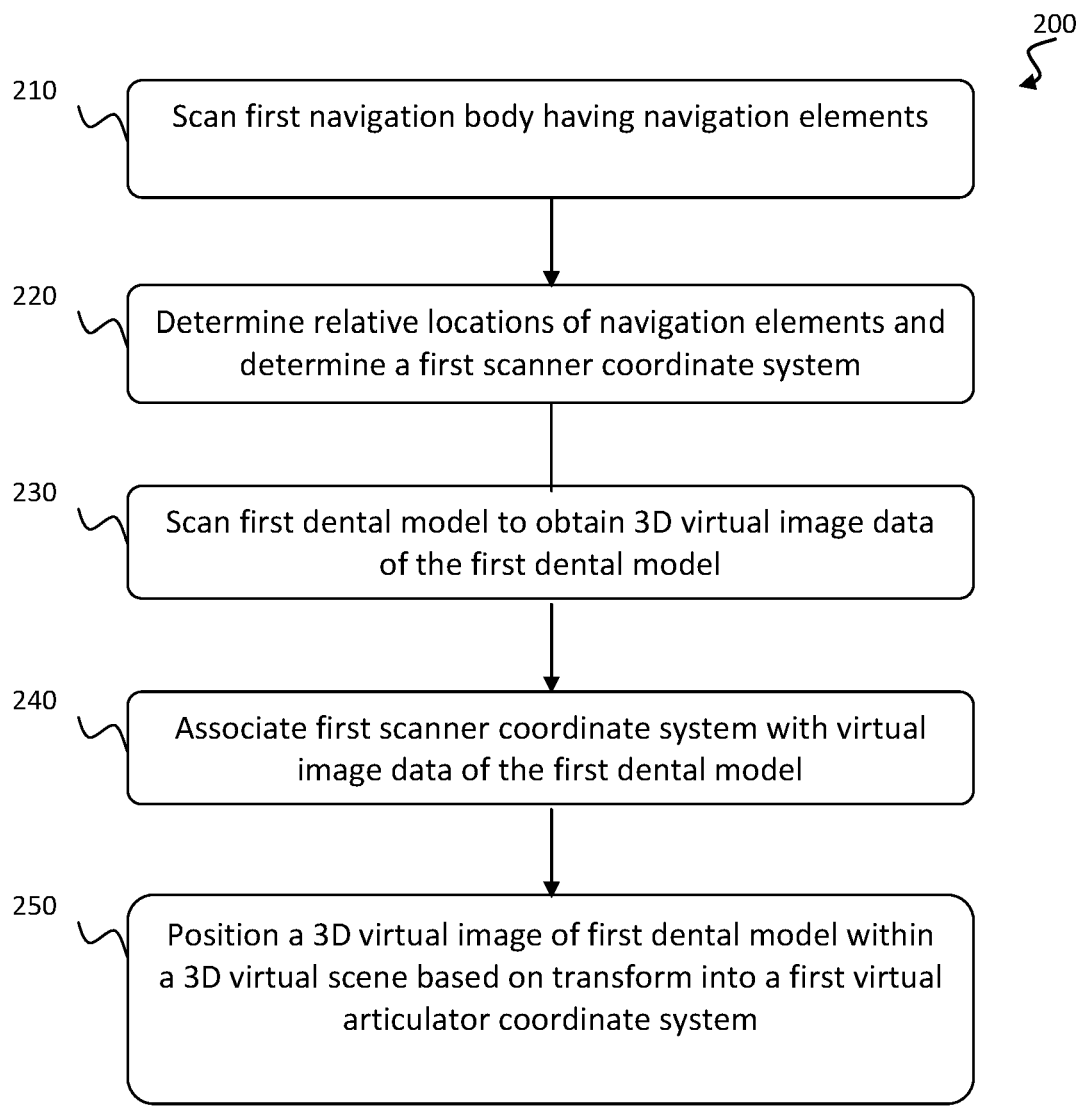
FIG. 5 shows a flowchart illustrating a method according to an embodiment of the present disclosure.

With reference to the flow chart 200 of FIG. 5, in one embodiment of the present disclosure there is provided a dental method that includes, at 210 scanning a first navigation body using a scanner, the first navigation body comprising a plurality of first navigation elements; at 220, determining the relative locations of the first navigation elements and, based on the relative locations of the navigation elements, determining a first scanner coordinate system; at 230, scanning a first dental model using the scanner to obtain three-dimensional virtual image data of the first dental model; at 240, associating the first scanner coordinate system with the virtual image data of the first dental model; and at 250, positioning a three-dimensional virtual image of the first dental model based on the three-dimensional virtual image data within a three-dimensional virtual scene.

As discussed in more detail below, the three-dimensional virtual scene is associated with a first virtual articulator coordinate system, and the positioning of the virtual image of the first dental model within the virtual scene can comprise positioning and orienting the virtual image of the first dental model relative to the first articulator coordinate system based on a transformation of the virtual image data of the first dental model from the first scanner coordinate system to the articulator coordinate system.

In one embodiment, the navigation body 110, connector 120 and support body 130 described above are employed in the method of FIG. 5.

For example, with reference to FIG. 6, and in accordance with item 210 of FIG. 5, the navigation body 110 is engaged to the connector 120, located on the floor 141 of the scanner. The navigation body 110, including its navigation elements 114, is scanned and 3D scanning data for the navigation body is acquired.

Using computer-based feature extraction techniques, the centres of the navigation elements 114 in three-dimensional space are calculated from the scanning data and, based on the relative locations of the centres of the navigation elements, a first scanner coordinate system is determined, in accordance with item 220 of FIG. 5. The centres 114a of the three navigation elements 114 can provide three different points in space, with a notional plane extending through each point. The notional plane can define x- and y-axes of the first scanner coordinate system. A z-axis can be defined as an axis extending perpendicularly to the notional plane. The exact location and rotational position of the axes can be determined based on a positioning of a specific one or more of the navigation elements. In this regard, the navigation elements can be distinguished from each other. As illustrated in FIG. 7a, for example, the centres 114a of the navigation spheres 114 are positioned at vertices of a notional triangle 114b. The triangle 114b is non-equilateral and more specifically an isosceles triangle including two legs and a base. Thus, even when considered in isolation of the rest of the navigation body 110, the different navigation spheres 114 can be distinguished from each other and the first scanner coordinate system determined accordingly.

With reference to FIG. 7b, the scanner coordinate system 201 is illustrated schematically, relative to the navigation body 110, using a set of three perpendicular axes. The origin, or '0,0,0' point of the scanner coordinate system is provided at a scanner datum point 202. In this embodiment, the scanner datum point 202 is located roughly at the centre of the engagement surface 111 of the navigation body.

Figure 8:
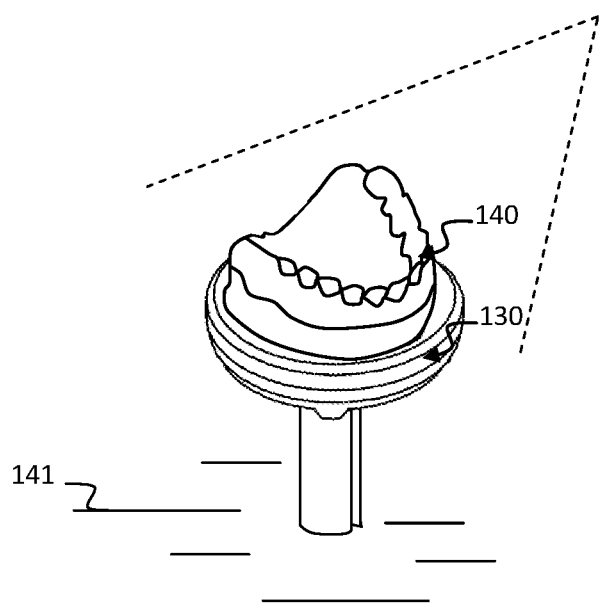
FIG. 8 shows a top oblique view of the support body and dental model of FIG. 4 mounted to the connector of FIG. 2 during scanning according to an embodiment of the present disclosure.

With reference to FIG. 8, and in accordance with item 230 of FIG. 5, the support body 130, including the first dental model 140 positioned thereon, is engaged to the connector 120, located on the floor 141 of the scanner or other surface of the scanner. The support body 120 and most importantly the dental model 140 are scanned and three-dimensional virtual image data of the first dental model 140 is acquired.

Figure 9:
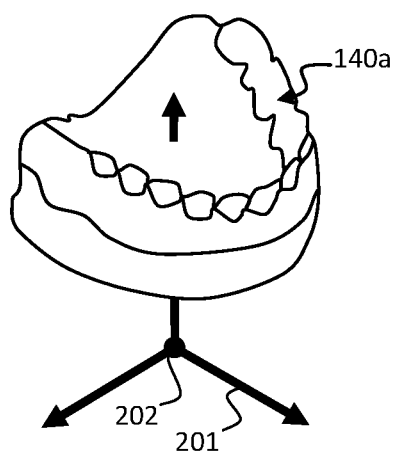
FIG. 9 shows a top oblique view of a virtual image of a dental model obtained during scanning, and associated with a scanner coordinate system, according to an embodiment of the present disclosure.

A three-dimensional virtual image 140a of the first dental model 140, based on the three-dimensional virtual image data, is illustrated in FIG. 9. In accordance with item 240 of FIG. 5, the first scanner coordinate system 201 is associated with the virtual image data of the first dental model 140 (e.g. as part of a single data packet), which coordinate system 201 is also represented visually in FIG. 9. Since the first navigation body 110 and first the dental model 140 are mounted to the same connector 120 during their respective scans, and at corresponding orientations, the first scanner coordinate system 201 obtained using the first navigation body 110 is applicable to the three-dimensional virtual image data of the first dental model.

Figure 10:
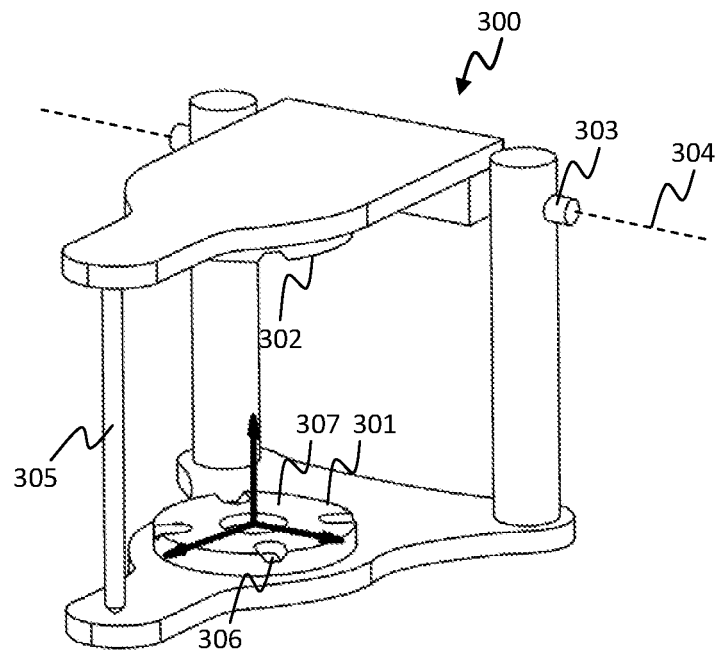
FIG. 10 shows a top oblique view of a physical articular that can be used in relation to an embodiment of the present disclosure.

As discussed above, embodiments of the present disclosure relate to a dental method in which virtual images of dental models are positioned in a virtual scene relating to an articulator. A drawing of a physical (real-world) articulator 300 that can form part of the apparatus of the present embodiment is provided in FIG. 10. The articulator 300 includes a lower jaw plate 301 and an upper jaw plate 302 on which upper and lower dental models, e.g. while located on respective support bodies 130, can be respectively mounted. The articulator 300 includes a hinge mechanism 303 that enables the lower and upper jaw plates to relatively rotate about a hinge axis 304, the hinge axis 304 replicating the hinge axis of the mandibular condyles of a jaw. The articulator 300 also includes an incisal guide pin 305 that is connected to the upper jaw plate 302 and extends vertically towards the lower jaw plate 301. The pin 305 is configured to maintain an established vertical separation of the upper and lower jaw plates 301, 302. Each of the lower and upper jaw plates 301, 302 includes a receiving surface 307 that is configured in a substantially identical manner to the receiving surface 121 of the connector 120. For example, the receiving surface 307 of the lower and upper jaw plates 301, 302 includes a plurality of recesses 306 for engaging with the complimentary protrusions 134 of the support body 130. The arrangement of protrusions 134 and recesses 306 ensures that the support body 130 is positionable at one desirable orientation on each plate 301, 302 of the articulator 300 and prevents lateral movement of the support body 130 relative to the connector 120 when engaged. In general, the articulator 300 can hold support bodies 130 securely, in a fixed location, while a bite relationship of the dental models can be tested, for example.

It is desirable to accurately replicate features of the articulator 300, with one or more dental models mounted thereon, in the virtual scene. Accurately replicating features of the articulator 300, along with one or more dental models, virtually, means that virtual design processes can be carried out that can also be matched and tested on the physical articulator 300.

Figure 11:
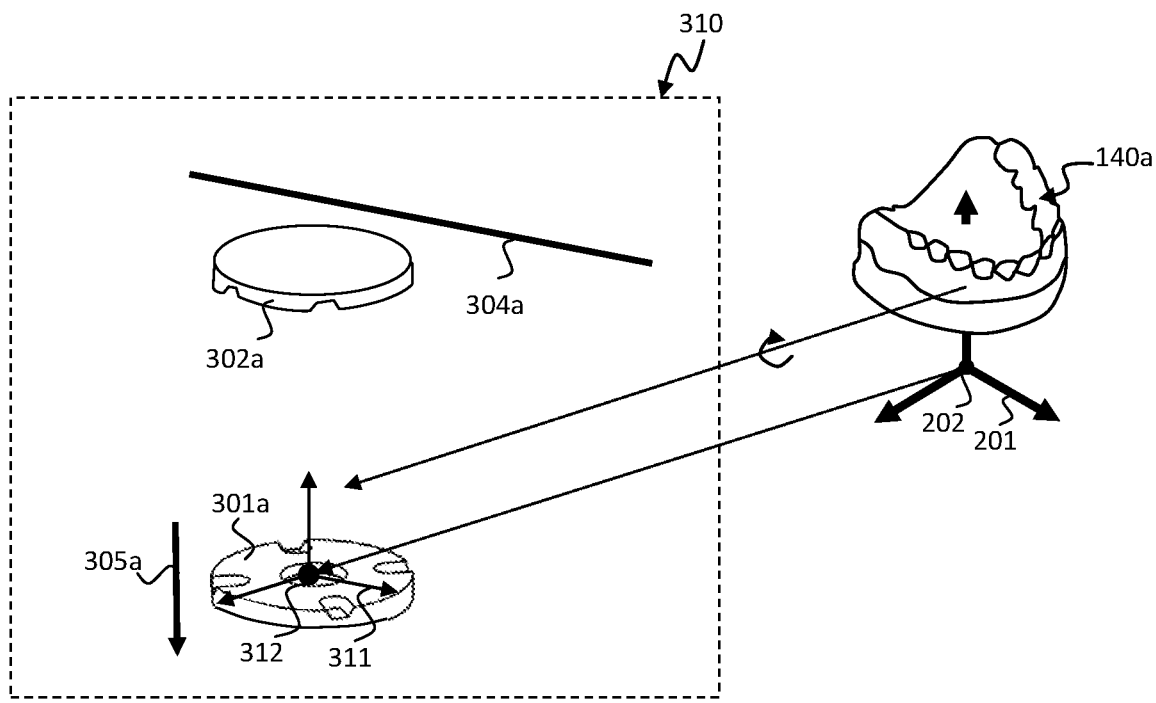
FIG. 11 shows a virtual image of parts of the articulator of FIG. 10 and a schematic illustration of how the virtual image of the dental model of FIG. 9 is located within the virtual image of the parts of the articulator.

In accordance with this, FIG. 11 shows a three dimensional virtual scene including a virtual image 310 of features of the physical articulator 300, including portions 301a, 302a representing the lower and/or upper plates 301, 302, a representation 304a of the hinge axis 304, and a representation 305a of a distal end of the pin 305.

The three-dimensional virtual scene is associated with a first virtual articulator coordinate system 311. The first virtual articulator coordinate system 311 is illustrated schematically in FIG. 11 using a set of three perpendicular axes. The origin, or '0,0,0' point of the first virtual articulator coordinate system 311 is provided at a first virtual articulator datum point 312. In this embodiment, the first articulator datum point 312 is located roughly at the centre of the receiving surface of the lower plate 301a.

In accordance with item 250 of FIG. 5, and also as represented schematically in FIG. 11, the three-dimensional virtual image 140a of the first dental model 140 is positioned within the virtual scene and specifically, in this embodiment, within the three-dimensional virtual image 310 of the at least part of the articulator 300. The positioning involves orienting the virtual image 140a of the first dental model 140 within the virtual image 310 based on a transformation of the virtual image data of the first dental model from the first scanner coordinate system 201 to the first virtual articulator coordinate system 311. The transformation aligns the first scanner datum point 202 exactly upon the first virtual articulator datum point 312 and aligns the axes of the scanner coordinate system 202 to match the corresponding axes of the virtual articulator coordinate system 311. The translation positions and orients the virtual image 140a of the dental model 140a appropriately within the virtual image 310 of the at least part of the articulator 300.

The translation can rely on software-based image registration techniques known to a person skilled in the art to transform different sets of data into a single coordinate system, for example, and may employ transformation models including linear transformations, for example.

Figure 12:
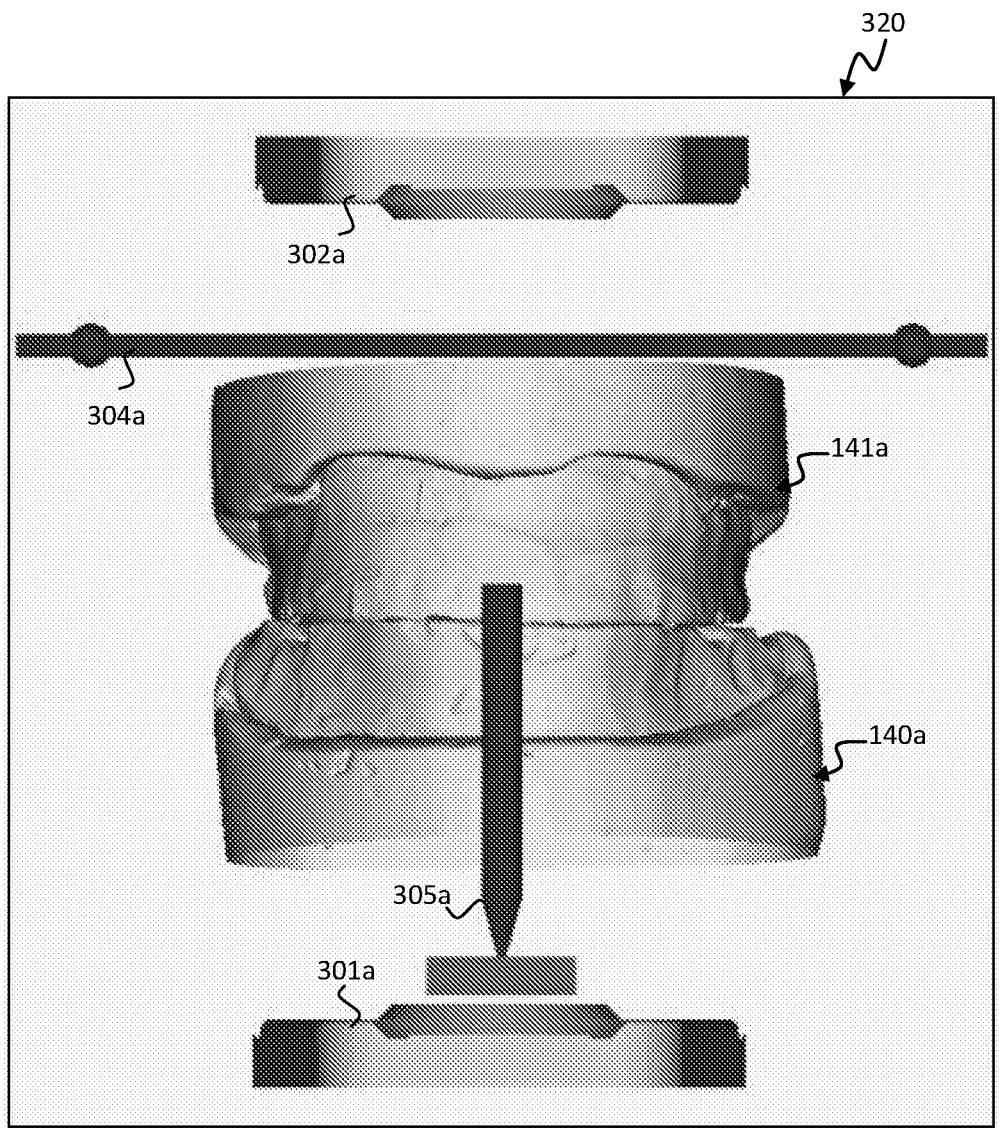
FIG. 12 shows a screenshot of a virtual image within a CAD software package.

The three-dimensional virtual image 310 of the articular and dental model can be provided within, and further manipulated using, computer-aided-design (CAD) software. A screenshot 320 of such a virtual image within a CAD software package is shown in FIG. 12. In the screenshot, in addition to the three-dimensional virtual image 140a of the first dental model, and virtual features 301a, 302a, 304a, 305a of the articulator, a three dimensional image 141a of a second dental model is provided. In this embodiment, the second dental model is a cast of the gums and teeth of an upper jaw.

The virtual image can be presented on a display such as a computer screen, tablet screen, smartphone screen or other types of displays suitable for presenting digital images.

To provide the three-dimensional virtual image of the second dental model, some or all of the steps, discussed with reference to FIG. 5, for example, are repeated.

Thus, the method can comprise scanning the second dental model in a manner, e.g. as described with reference to FIGS. 8 and 9, to obtain three-dimensional virtual image data of the second dental model. The image data can then be associated with the first scanner coordinate system, in the manner described above, or with a different, second scanner coordinate system.

The same, first scanner coordinate system can be associated with the three-dimensional virtual image data of the second dental model by mounting the second dental model to the same connector 120 within the scanner and in the same manner. The same scanner coordinate system is therefore applicable to both models.

Nevertheless, it can be advantageous to determine a second scanner coordinate system, e.g., to maintain a high level of accuracy over time. If environmental factors in the scanner change, e.g., as a result of placing the different dental models in the scanner, determining a second scanner coordinate system that is specific to the second dental model can improve accuracy. Changes in environmental factors can include slight movements in the connector on which the dental models are mounted, or relative movement of other scanner parts.

When a second scanner coordinate system is used, the method can comprise scanning again the first navigation body 110 using the scanner and determining the second coordinate system in the same manner that the first coordinate system 201 is determined. Alternatively, a second navigation body can be used that is similar or identical to the first navigation body 110, with the second coordinate system being determined in substantially the same manner as the first coordinate system.

Figure 13:
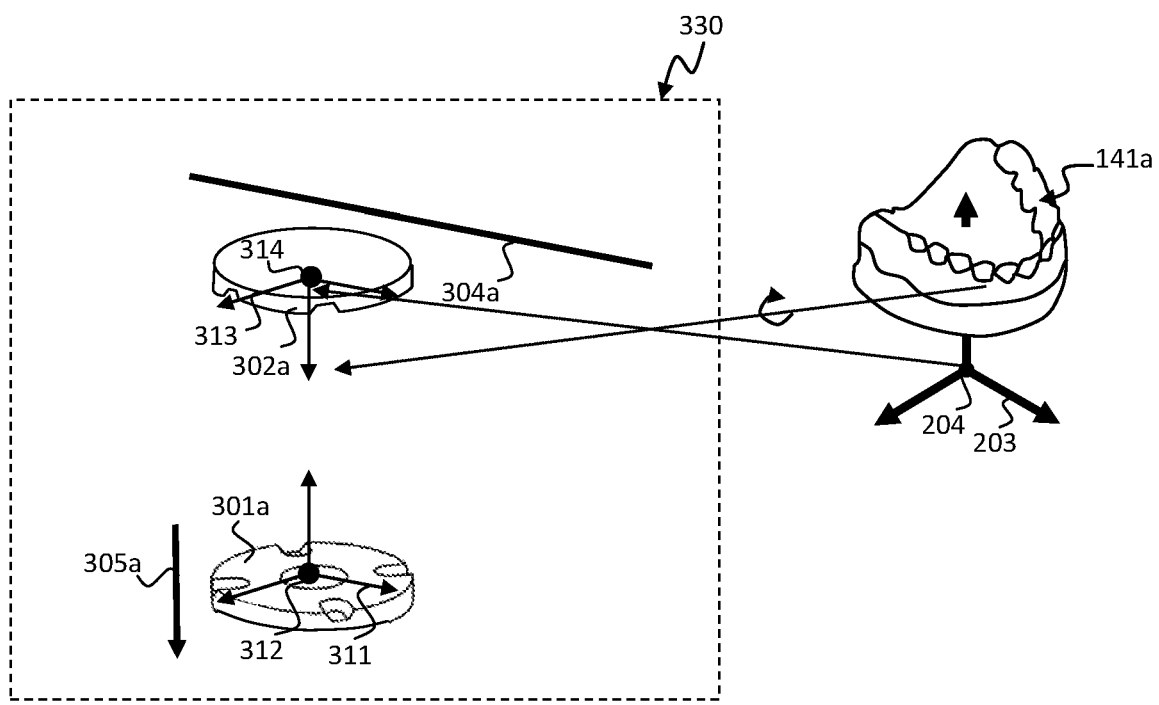
FIG. 13 shows a virtual image of parts of the articulator of FIG. 10 and a schematic illustration of how the virtual image of a second dental model is located within the virtual image of the parts of the articulator.

FIG. 13 shows a three dimensional virtual scene including a virtual image 330 of features of the physical articulator 300, including representations 301*a*, 302*a* of the lower and/or upper plates 301, 302, a representation 304*a* of the hinge axis 304, and a representation 305*a* of a distal end of the pin 305. The image 330 of FIG. 13 is similar to the image 310 of FIG. 11. However, in this instance, the image 330 is also associated with a second virtual articulator coordinate system 313 in addition to the first virtual articulator coordinate system 311. The second virtual articulator coordinate system 313 is again illustrated schematically in FIG. 13 using a set of three perpendicular axes. The origin, or '0,0,0' point of the second virtual articulator coordinate system 311 is provided at a second virtual articulator datum point 314. In this embodiment, the second articulator datum point 314 is located roughly at the centre of the receiving surface of the upper plate 302*a*.

In accordance with item 250 of FIG. 5, and also as represented schematically in FIG. 13, the three-dimensional virtual image 141*a* of the second dental model is positioned within the virtual scene and specifically, in this embodiment, within the three-dimensional virtual image 330 of the at least part of the articulator 300. The positioning involves orienting the virtual image 141*a* of the second dental model within the virtual image 330 based on a transformation of the virtual image data of the second dental model from the second scanner coordinate system 203 (or, if used instead the first scanner coordinate system 201) to the second virtual articulator coordinate system 313. The transformation aligns the respective scanner datum point 202, 204 exactly upon the second virtual articulator datum point 314 and aligns the axes of the scanner coordinate system 201, 203 to match the corresponding axes of the second virtual articulator coordinate system 313. The translation positions and orients the virtual image 141*a* of the second dental model appropriately within the virtual image 330 of the at least part of the articulator 300.

Nevertheless, to position the three-dimensional virtual image of the second dental model in the virtual space within the three-dimensional virtual scene, alternative approaches may be taken. For example, the virtual image data of the second dental model may be transformed from the associated first or second scanner coordinate system to the first virtual articulator coordinate system, rather than any second virtual articulator coordinate system. However, a further translation can be applied to the virtual image data in order to shift the position of the virtual image of the second dental model so that it is adjacent the opposite jaw of the articulator. The further translation may be based on a known distance between the upper and lower jaws of the articulator, for example.

Further variations and/or modifications may be made to the above-described embodiments.

For example, while components of an articulator are represented visually in the images 310, 330 of FIGS. 11 and 13, in alternative embodiments, no visual representation of the components of the articulator may be provided. The virtual scene may include images of the dental model(s) and include background data relating to components of the articulator such as one or more of: the relative locations of all or part of a virtual lower jaw and/or a virtual upper jaw of the articulator; the shape and dimensions of all or part of the virtual lower jaw and/or the virtual upper jaw of the articulator; a virtual hinge position (hinge axis) of the articulator; and a virtual pin position of the articulator, along with rules of movement and interaction between these components. Based on this background data, the images of the dental model(s) may still be manipulated within the virtual scene in a manner representative of how the model(s) may be manipulated when mounted on the corresponding physical articulator.

As another example, the scanner coordinate systems can be determined using the navigation bodies after scanning of the dental models, rather than before scanning of the dental models.

As another example, each dental model may be mounted on a navigation body and collectively mounted to the connector in the dental scanner, prior to and during the scanning. By having the dental model connected to the navigation body, the scanning of the navigation body and the scanning of the dental model can take place at the same time. In this alternative approach, use of the support body may become redundant. Essentially, the navigation body can also act as a support body for the dental model. This enables the relative locations of the navigation elements, and thus the respective coordinate system, to be determined substantially at the same time as the three-dimensional virtual image data of the dental model is obtained.

A navigation body 150 according to an embodiment of the present disclosure, which also acts as a support body for the dental model, is illustrated in FIGS. 14*a* to 14*c*. The navigation body 150 has a generally plate-like configuration with an engagement surface 151 on a first side and a support surface 152 on a second side opposite to the first side. The navigation body 150 is substantially disk-shaped with a substantially circular periphery 153, although other shapes of the navigation body 150 can be used (e.g., square, rectangular or otherwise).

The navigation body 150 includes a plurality of navigation elements and, more particularly, three navigation spheres 154. The navigation spheres 154 are mounted partially in recesses in the support surface 152. The three navigation spheres 154 are spaced from each other and positioned at the vertices of a notional triangle. The navigation spheres 154 are spaced around the edges of the support surface 152 such as to leave an open region of the support surface 152 to receive a dental model 140. While navigation spheres 154 are used in this embodiment, a variety of different types of navigation elements may be used.

The engagement surface 151 of the navigation body 150 is configured to engage with a receiving surface of a connector of a scanner and of a plate of an articulator, e.g. in a similar manner to that described above.

The methods described above can rely in part on a common interface (e.g. based on common engagement and receiving surfaces) between different components, such as the navigation body 110, connector 120, support body 130 and articulator 300. To this end, a kit can be provided that includes, e.g. two or more of the navigation body 110, connector 120, support body 130 and articulator 300 that are specifically matched to each other in this manner.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A dental method for visualizing bite and teeth function comprising:
 a. determining a first scanner coordinate system, where the coordinate system is defined by perpendicular axes having an origin at the intersection of said perpendicular axes, by scanning a first navigation body with three navigation elements on a first support in a three-dimensional scanner;
 b. obtaining first three-dimensional virtual image data of a first dental model by scanning the first dental model in the three-dimensional scanner on the first support;
 c. associating the first scanner coordinate system with the first three-dimensional virtual image data in a three-dimensional virtual environment in a computer to obtain a three-dimensional virtual image of the first dental model; and
 d. creating a virtual scene by positioning and orienting the three-dimensional virtual image of the first dental model in a virtual articulator having a first virtual articulator coordinate system, defined by perpendicular axes having an origin at the intersection of said perpendicular axes, by transforming the virtual image data of the first dental model from the first scanner coordinate system to the first virtual articulator coordinate system.

2. The method of claim 1, wherein the first dental model is connected to the first navigation body, and the first navigation body and the first dental model are scanned at the same time.

3. The method of claim 1, wherein the transformation of the virtual image data of the first dental model from the first scanner coordinate system to the first virtual articulator coordinate system further comprises:
 a. a first scanner datum point, wherein the first scanner datum point is the origin of perpendicular axes of said first scanner coordinate system;
 b. wherein the first virtual articulator coordinate system comprises a first virtual articulator datum point, wherein the first virtual articulator datum point is the origin of perpendicular axes of the first virtual articulator coordinate system; and
 c. wherein positioning and orienting the three-dimensional virtual image of the first dental model in the virtual articulator comprises (i) superimposing the first scanner datum point exactly on the first virtual articulator datum point, and (ii) rotating the axes of the first scanner coordinate system to align with the axes of the first scanner coordinate system with the axes of the first virtual articulator coordinate system.

4. The method of claim 1, further comprising:
 a. determining a second scanner coordinate system by scanning a second navigation body with three navigation elements on a second support in a three-dimensional scanner;
 b. obtaining second three-dimensional virtual image data of a second dental model by scanning the second dental model in the three-dimensional scanner on the second support;
 c. associating the second scanner coordinate system with the second three-dimensional virtual image data in three-dimensional virtual environment in a computer to obtain a three-dimensional virtual image of the second dental model;
 d. positioning and orienting the three-dimensional virtual image of the second dental model in the virtual articulator having a second virtual articulator coordinate system, by transforming the virtual image data of the second dental model from the second scanner coordinate system to the second virtual articulator coordinate system; and
 e. wherein the virtual scene comprises positioning and orienting the second three-dimensional virtual image of the second dental model with the first three-dimensional virtual image of the first dental model in the virtual articulator.

5. The method of claim 1 further comprising manipulating the virtual scene with CAD software on the computer.

6. The method of claim 1 further comprising providing a dental procedure to a patient based on the virtual scene, wherein said dental procedure is selected from a diagnostic method, treatment planning, and prosthesis design and fabrication.

7. The method of claim 1 further comprising prosthesis design and fabrication using the virtual scene.

8. A dental method for visualizing bite and teeth function comprising:
 a. determining a first scanner coordinate system by scanning a first navigation body with three navigation elements on a first support in a three-dimensional scanner;
 b. obtaining first three-dimensional virtual image data of a first dental model by scanning the first dental model in the three-dimensional scanner on the first support, wherein the first dental model is connected to the first navigation body, and the first navigation body and the first dental model are scanned at the same time;
 c. associating the first scanner coordinate system with the first three-dimensional virtual image data in a three-dimensional virtual environment in a computer to obtain a three-dimensional virtual image of the first dental model; and
 d. creating a virtual scene by positioning and orienting the three-dimensional virtual image of the first dental model in a virtual articulator having a first virtual articulator coordinate system, by transforming the virtual image data of the first dental model from the first scanner coordinate system to the first virtual articulator coordinate system.

9. A dental method for visualizing bite and teeth function comprising:
 a. determining a first scanner coordinate system by scanning a first navigation body with three navigation elements on a first support in a three-dimensional scanner wherein said first scanner coordinate system is defined by perpendicular axes having an origin at the intersection of said perpendicular axes;

b. obtaining first three-dimensional virtual image data of a first dental model by scanning the first dental model in the three-dimensional scanner on the first support, wherein the first dental model is connected to the first navigation body, and the first navigation body and the first dental model are scanned at the same time;

c. associating the first scanner coordinate system with the first three-dimensional virtual image data in a three-dimensional virtual environment in a computer to obtain a three-dimensional virtual image of the first dental model;

d. creating a virtual scene by positioning and orienting the three-dimensional virtual image of the first dental model in a virtual articulator having a first virtual articulator coordinate system defined by perpendicular axes having an origin at the intersection of said perpendicular axes, by transforming the virtual image data of the first dental model from the first scanner coordinate system to the first virtual articulator coordinate system;

e. wherein the transformation of the virtual image data of the first dental model from the first scanner coordinate system to the first virtual articulator coordinate system further comprises:

i. a first scanner datum point, wherein the first scanner datum point is the origin of said perpendicular axes of the first scanner coordinate system;

ii. wherein the first virtual articulator coordinate system comprises a first virtual articulator datum point, wherein the first virtual articulator datum point is the origin of said perpendicular axes of the first virtual articulator coordinate system; and iii. wherein positioning and orienting the three-dimensional virtual image of the first dental model in the virtual articulator comprises (i) superimposing the first scanner datum point exactly on the first virtual articulator datum point, and (ii) rotating the axes of the first scanner coordinate system to align the axes of the first scanner coordinate system with the axes of the first virtual articulator coordinate system.

10. A dental method for visualizing bite and teeth function comprising:

a. determining a first scanner coordinate system by scanning a first navigation body with three navigation elements on a first support in a three-dimensional scanner;

b. obtaining first three-dimensional virtual image data of a first dental model by scanning the first dental model in the three-dimensional scanner on the first support, wherein the first dental model is connected to the first navigation body, and the first navigation body and the first dental model are scanned at the same time;

c. associating, in a three-dimensional virtual environment in a computer, the first scanner coordinate system with the first three-dimensional virtual image data to obtain a three-dimensional virtual image of the first dental model; and d. creating a virtual scene by positioning and orienting the three-dimensional virtual image of the first dental model in a virtual articulator having a first virtual articulator coordinate system, by transforming the virtual image data of the first dental model from the first scanner coordinate system to the first virtual articulator coordinate system.

11. A dental apparatus for visualizing bite and teeth function comprising:

a. A three-dimensional scanner and a computer with CAD software;

b. determining a scanner coordinate system by scanning a navigation body with three navigation elements on a support in the three-dimensional scanner;

c. obtaining three-dimensional virtual image data of a dental model by scanning the dental model in the three-dimensional scanner on the first support;

d. associating, in a three-dimensional virtual environment in the CAD software, the scanner coordinate system with the three-dimensional virtual image data to obtain a three-dimensional virtual image of the dental model;

e. creating a virtual scene by positioning and orienting the three-dimensional virtual image of the dental model in a virtual articulator having ac virtual articulator coordinate system, by transforming the virtual image data of the dental model from the first scanner coordinate system to the virtual articulator coordinate system; and f. displaying the virtual scene on a computer display.

* * * * *